United States Patent [19]
O'Donnell et al.

[11] Patent Number: 5,749,853
[45] Date of Patent: May 12, 1998

[54] INFLATION CONTROL SYSTEM WITH ELAPSED TIME MEASUREMENT

[75] Inventors: Joseph A. O'Donnell; Douglas R. Hamper, both of Escondido, Calif.

[73] Assignee: Advanced Cardiovascular Systems, Inc., Santa Clara, Calif.

[21] Appl. No.: 406,202

[22] Filed: Mar. 17, 1995

[51] Int. Cl.[6] .................... A61M 29/00; A61M 1/00
[52] U.S. Cl. ............................................. 604/97
[58] Field of Search .................. 604/99–100, 30–34, 604/65–67, 118

[56] References Cited

U.S. PATENT DOCUMENTS

| | | | |
|---|---|---|---|
| 4,106,002 | 8/1978 | Hogue, Jr. ................... | 340/626 |
| 4,694,409 | 9/1987 | Lehman ....................... | 364/558 |
| 5,004,472 | 4/1991 | Wallace ....................... | 606/194 |
| 5,009,662 | 4/1991 | Wallace et al. ............. | 606/192 |
| 5,021,046 | 6/1991 | Wallace ....................... | 604/97 |
| 5,084,060 | 1/1992 | Freund et al. .............. | 606/192 |
| 5,135,488 | 8/1992 | Foote et al. ................ | 604/97 |
| 5,201,753 | 4/1993 | Lampropoulos et al. ... | 606/192 |
| 5,215,523 | 6/1993 | Williams et al. ........... | 604/97 |
| 5,300,027 | 4/1994 | Foote et al. ................ | 604/100 |

*Primary Examiner*—Manuel Mendez
*Attorney, Agent, or Firm*—Fulwider Patton Lee & Utecht, LLP

[57] ABSTRACT

The time duration of the inflation and deflation cycles for a syringe assembly for an inflation system are measured and displayed. An inflation cycle is initiated when a increase-pressure switch is depressed. A timer will begin timing the inflation cycle when the increase-pressure switch is released and a predetermined initial pressure is detected in a tube of the syringe assembly. A deflation cycle is initiated when a decrease-pressure switch is depressed. The timer will stop measuring the inflation cycle and then begin timing the deflation cycle when the decrease-pressure switch is released and a predetermined neutral pressure is detected in a tube of the syringe assembly. Rapid deflation can be achieved by depressing a rapid-decrease-pressure switch. Upon actuation of the rapid-decrease-pressure switch, the timer immediately stops measuring the inflation cycle and begins timing the deflation cycle.

13 Claims, 13 Drawing Sheets

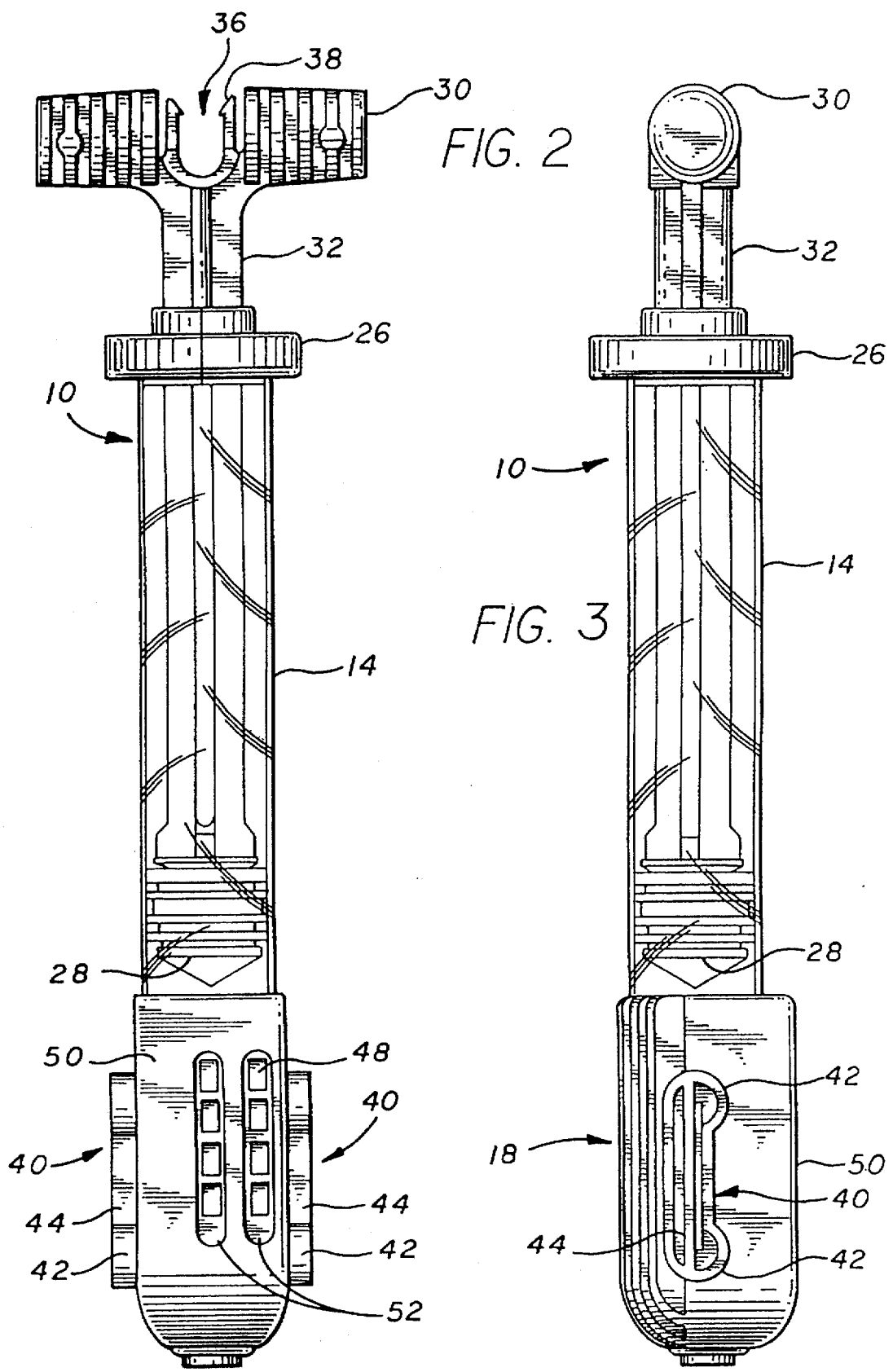

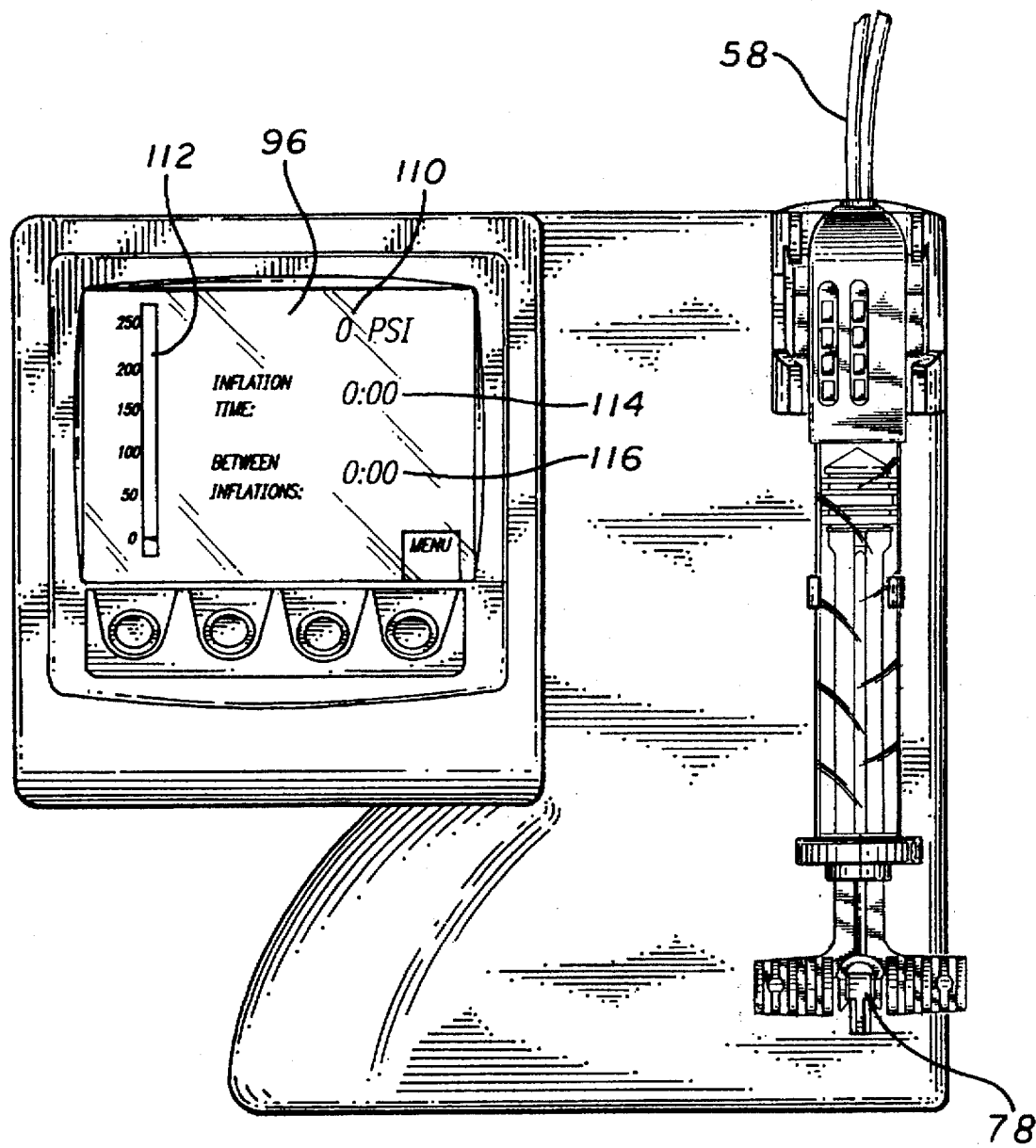

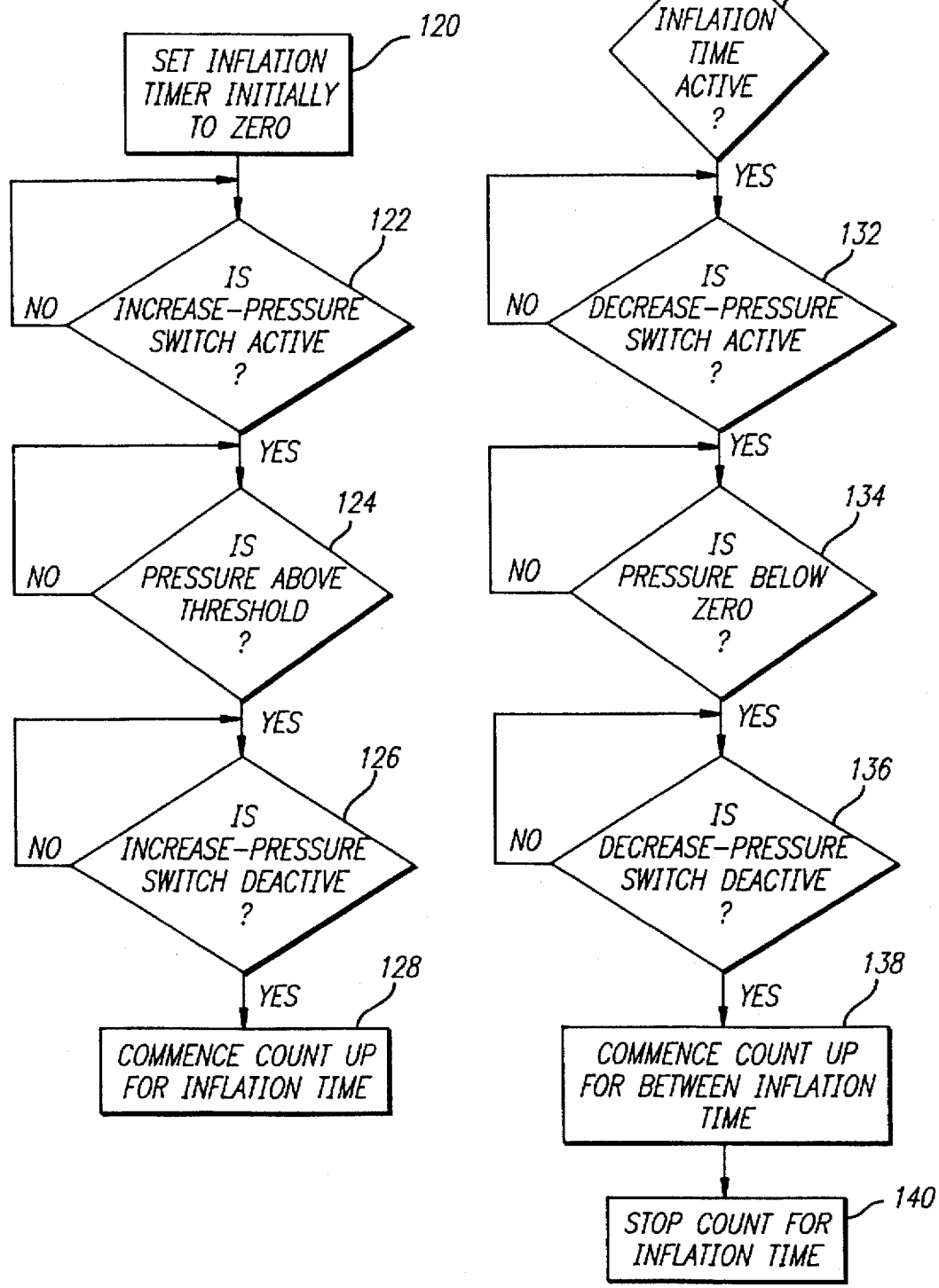

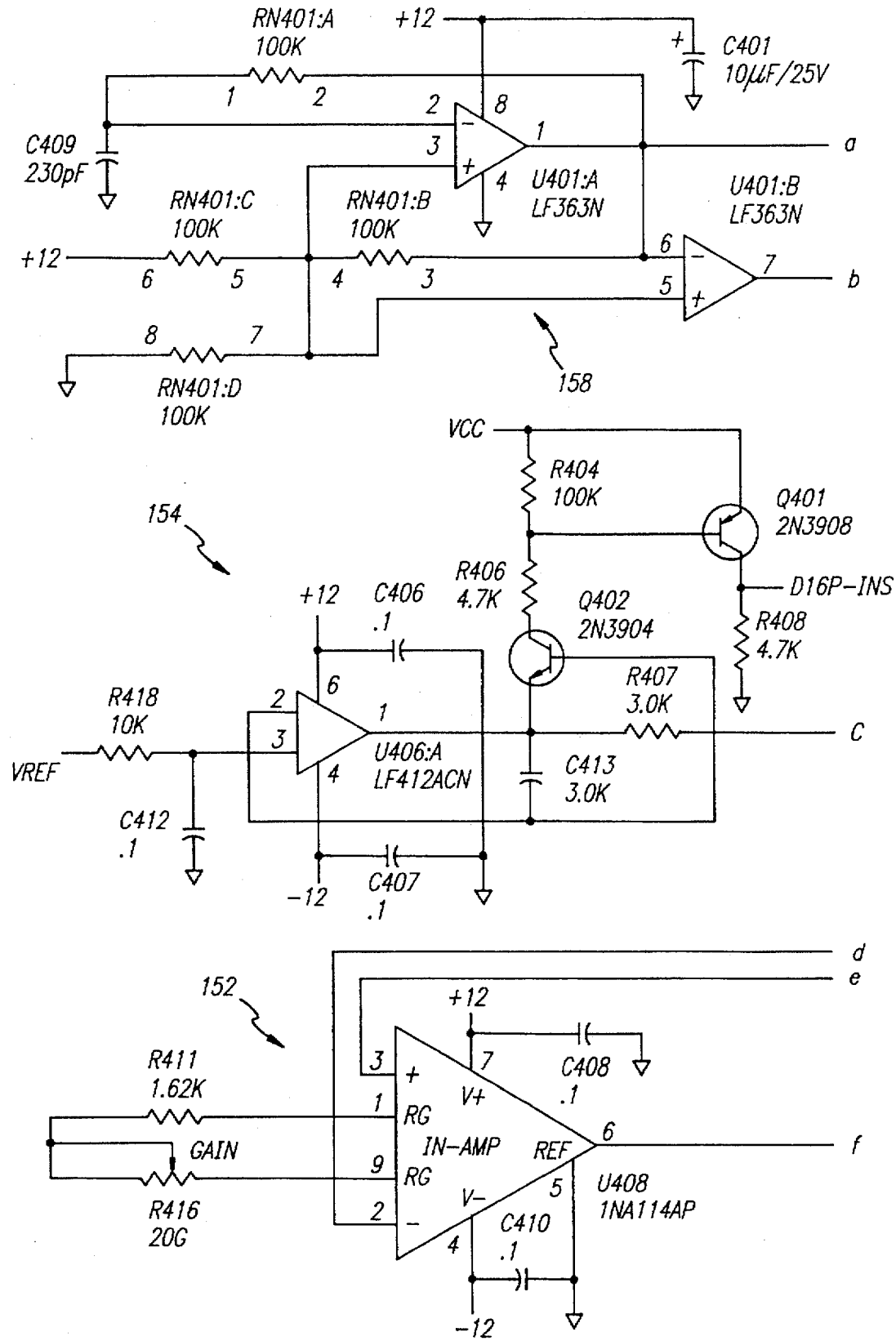

INFLATION CONTROL SYSTEM WITH ELAPSED TIME MEASUREMENT

BACKGROUND

The invention generally relates to inflation devices used in medical procedures, and more particularly, to inflation control systems suitable for controlling the inflation and deflation of balloons or other inflatable devices used in medical procedures, such as balloon catheters used in angioplasty procedures.

Dilatation balloon catheters have been used in increasing numbers in angioplasty procedures to dilate or enlarge blood vessels that have been partially or almost completely blocked by stenosis (a narrowing of the vessel due to injury or disease). Angioplasty procedures have been used to treat stenoses in coronary arteries, peripheral arteries, urethral passages, fallopian tubes, etc. Particularly, the procedure for dilating coronary arteries, referred to as percutaneous transluminal coronary angioplasty (PTCA), has provided an effective and less traumatic treatment technique than coronary by-pass surgery or other surgical treatment methods.

In a typical angioplasty procedure, a guiding catheter is percutaneously introduced into the vascular system of a patient and is directed to a point near the site of the stenosis. Subsequently, a guidewire and a dilatation catheter having an inflatable balloon mounted on the distal end thereof are introduced through the guiding catheter with the guidewire slidably disposed within an inner lumen of the dilatation catheter. The guidewire is advanced out of the distal end of the guiding catheter and is maneuvered into the patient's vasculature containing the stenosis to be dilated, and is then advanced beyond the stenosis. Thereafter, the dilatation catheter is advanced over the guidewire until the dilatation balloon is located across the stenosis. Once in position, the dilatation balloon is inflated to a predetermined size, typically the same size as the inner diameter of the blood vessel at that location, by radiopaque liquid at relatively high pressures (e.g., generally greater than about four atmospheres). The inflated, pressurized balloon radially compresses the atherosclerotic plaque of the stenosis against the inside of the vessel wall to thereby dilate the lumen of the vessel and allow increased blood flow through the vessel.

In a typical PTCA procedure, the balloon is inflated and deflated several times with the pressure maintained for several seconds during each inflation, until the desired patency in the blood vessel is obtained. The physician typically monitors a timing device to control the duration of each inflation and the duration between inflations. Each inflation of the balloon interferes with the blood supply circulation; therefore, the duration must be kept as short as possible, yet must still be long enough to obtain the results desired. The duration between inflations is monitored to allow enough time for the blood supply to reestablish itself before the next inflation. After the procedure has been completed, the balloon is deflated for the final time and maintained under negative pressure so that the dilatation catheter can be withdrawn from the patient and the blood flow resumed through the dilated vessel.

To inflate or deflate the balloon, the physician typically uses an inflation device, such as a syringe, placed in fluid communication with the interior of the balloon. The physician uses one hand to grasp the syringe body and the other hand to maneuver the plunger to pressurize or depressurize the inflation fluid as required. Manually operated syringe-type inflation systems of the type described are manufactured and sold by Advanced Cardiovascular Systems, Inc. of Santa Clara, Calif. under the trademark INDEFLATOR.

Such manual inflation systems have proven to be of great value in conducting angioplasty procedures. Some systems include a pressure sensor with a display that indicates to the operator the fluid pressure in the catheter and balloon. A balloon pressure display allows the physician to monitor whether the arterial plaque causing the stenosis is subjected to a sufficiently high pressure to cause compression of the plaque. Such a display also allows the physician to monitor the pressure to ensure that the balloon pressure limits specified by the manufacturer are not exceeded. Furthermore, if the pressure display indicates a sudden and unexpected decrease in pressure, the physician may be alerted so that any necessary remedial action can be taken.

However, manual systems typically require the physician to use both hands to control the inflation and deflation processes. Each time an adjustment in the location of the balloon in the patient's vessel must be made, the physician must move at least one hand from the inflation control system to the catheter to accomplish the relocation of the balloon, and must then return to the inflation system with both hands. Rather than having to use both hands on the inflation device, it would be preferable for the physician to only use one hand thereby leaving the second hand free to control the position of the catheter in the vessel or to perform other tasks, as needed.

A further consideration with manual inflation systems is the ease with which the system can be used. In manual systems that require a substantial amount of hand strength to maneuver the syringe plunger for developing enough pressure in the balloon to compress the plaque, the physician may experience hand fatigue as a result of operating such an inflation device for several inflation and deflation cycles, each lasting several seconds.

Inflation control systems using a motor drive to control the position of a plunger in a syringe to control the balloon pressure have been described. Such motor drive inflation systems reduce or eliminate the need for the physician to manually control the position of the plunger in the syringe. The physician instead controls the movement of a motor through an electrical switch. That motor performs the work of moving the syringe plunger. Usually only one hand is needed to operate the electrical switch or switches needed for motor control thus leaving one of the physician's hands free to locate the catheter or perform other tasks. Such systems can provide the ability to inflate or deflate the balloon catheter at a precise moment during the maneuvering of the catheter in the patient's vessel with relatively precise control over the rates of inflation and deflation and the amount of pressure in the balloon.

Once the balloon catheter is in place in the patient's vessel, the balloon is inflated, typically for 60 to 120 seconds, although the times can be extended through the use of a perfusion catheter. The inflation time is limited because during inflation, the flow of blood to the heart is stopped thereby increasing the possibility of cardiac arrest. It is therefore important for the physician to monitor the elapsed time that the balloon has been inflated. The balloon is then deflated and may then be reinflated. The balloon may be inflated and deflated a number of times during a procedure as this allows more accumulated inflation time, but reduces the length of time that the blood flow is cut off at any one inflation cycle, with a corresponding reduction in ischemia that would otherwise result if a single longer inflation were used.

In the case where multiple cycles of inflations and deflations are used in the procedure, the physician typically desires to also know the elapsed time between inflations. A minimum time of deflation is usually allowed to expire before reinflating the balloon so that sufficient blood flow can reach the heart before it is once again cut off.

In some prior systems, a pressure gauge displaying the pressure developed in the balloon was provided; however, determining the elapsed time of the inflation had to be accomplished by resort to another device, such as a separate stopwatch or a wall clock. The use of such a separate device could prove distracting as well as require extra effort to perform the timing function. It would be preferable to integrate the timing function with the inflation control system and present an elapsed time display adjacent the pressure display so that the physician need only observe a single display to see both pressure and timing data.

Automated timing systems have been disclosed in which the elapsed time of an inflation and the time between inflations are based solely on the pressure in the inflation device crossing a threshold pressure. In some cases however, the physician prefers greater control over the beginning and ending of the timing period. Manual control is preferred in some cases. For example, the physician may desire to begin the inflation duration timing only after the balloon has become completely inflated at a relatively high pressure. Conversely, the physician may desire to begin timing the period of time between inflations only after the pressure has decreased below one atmosphere or upon the manual movement of a switch.

Hence those skilled in the art have recognized the need for a motor driven inflation system combined with a timing system so that the physician need only view a single display to obtain both timing and pressure data. Additionally, the need has also been recognized for greater control over the commencement and the cessation of the timing function. The present invention fulfills these needs and others.

SUMMARY OF THE INVENTION

The invention is directed to a system for controlling the inflation of an inflatable device and for measuring the elapsed time during selected periods of inflation control. In one aspect, the system comprises an inflation medium disposed in the inflatable device, the extent of inflation controlled by the pressure of the inflation medium; a pressure control device that controls the pressure of the inflation medium in response to pressure control signals; a sensor that senses the pressure of the inflation medium and provides a pressure sense signal; a manually operable pressure-decrease switch that provides a pressure decrease control signal to the pressure control device; a manually operable pressure-increase switch that provides a pressure increase control signal to the pressure control device; a timer that measures elapsed time and provides a time signal; and a display that receives the time signal and displays the elapsed time based on the time signal.

In another aspect, the timer begins timing elapsed time of the inflation only after a pressure control switch that has previously been activated is deactivated after the pressure exceeds a predetermined level. The display displays the elapsed inflation time. The timer stops timing the inflation period when a pressure control switch that has previously been activated is deactivated below a predetermined pressure level.

In a further aspect, a timer provides the time between inflations when the pressure in the system has exceeded a first predetermined pressure level and then a pressure control switch that has previously been activated is deactivated below a second predetermined pressure level. In a further aspect, this time is displayed as the time between inflations.

In yet a further aspect, the system includes a rapid pressure-decrease switch. A timer begins timing elapsed time between inflations at the time the rapid pressure-decrease switch is deactivated. In a more detailed aspect, elapsed timing of time between inflations does not occur unless a timer is presently timing an inflation.

These and other features and advantages of the invention will become more apparent from the following detailed description, taken in conjunction with the accompanying exemplary drawings.

BRIEF DESCRIPTION OF THE DRAWINGS

FIG. 2 is a top view of the syringe and pressure sensor of the syringe assembly of FIG. 1;

FIG. 3 is a side view of the syringe and pressure sensor of the syringe assembly of FIG. 1;

FIG. 11 is a front view of an inflation control system showing a front panel display;

FIG. 12 is a flow chart illustrating the determination of the elapsed time of an inflation cycle;

FIG. 13 is a flow chart illustrating the determination of the elapsed time between inflation cycles;

FIGS. 16A and 16B are circuit diagrams of instrument circuitry responsive to remote controller signals, pressure signals, and which provide isolation for the remote controller.

DETAILED DESCRIPTION OF THE PREFERRED EMBODIMENTS

Figure 1:
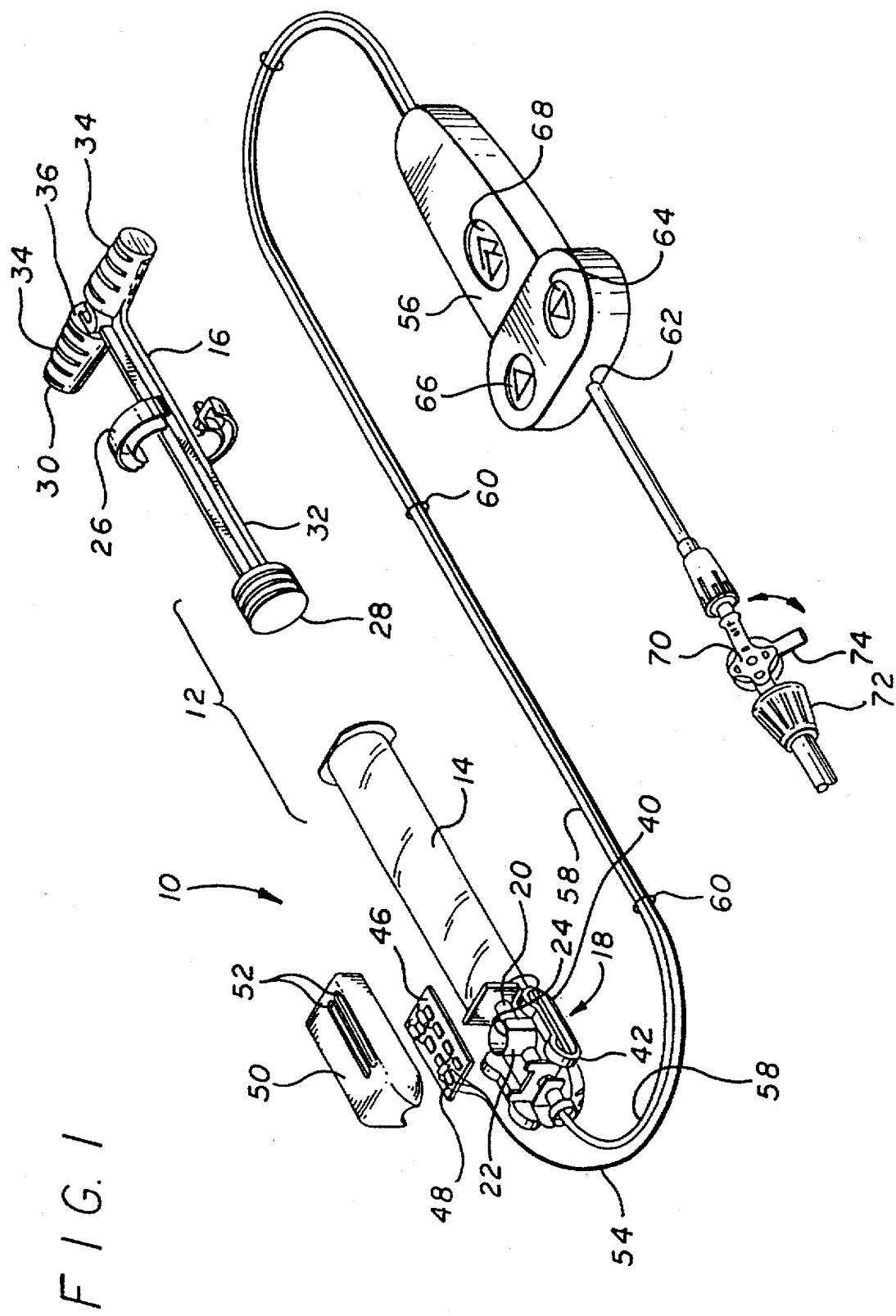
FIG. 1 is a partially exploded view of a syringe assembly having a syringe, fluid tubing, and a pressure sensor mounted to the fluid tubing to sense the fluid pressure in that tubing.

Referring now to the drawings in which like reference numerals designate like or corresponding features among the several views, FIGS. 1 through 3 illustrate a syringe assembly 10 in accordance with one embodiment of the present invention. The syringe assembly 10 includes a syringe 12 having a syringe barrel 14, or other fluid chamber, and a plunger 16 disposed at one end of the syringe barrel 14 for altering the volume in the syringe barrel depending on the position of the plunger 16 in the barrel 14. The syringe assembly also includes a mounting head 18 disposed at the opposite or distal end of the syringe barrel from the plunger. Fluid tubing 20 is coupled to the distal opening in the barrel for conducting inflation fluid to and from the syringe barrel. The rigid tubing 20 provides fluid communication with a downstream flexible tubing 58 that may be made of any suitable material that can withstand the pressures associated with the inflation and deflation of a balloon catheter or other inflatable device. The preferred material suitable for the flexible tubing 58 is polyurethane with a braided nylon. Other possible materials are PVC or flexible copolymers.

A sensor port 22 and a pressure sensor 24 are mounted to the fluid tubing 20. The sensor port is in fluid communication with the fluid tubing and therefore the pressure sensor provides an indication of the fluid pressure in the fluid tubing 20. The pressure sensor 24 can be a strain beam type sensor or a piezo-resistive transducer or other types.

The plunger 16 includes a plunger retainer 26 that maintains the plunger at a selected orientation within the syringe barrel 14. The plunger further includes a movable piston 28 that controls the size of the volume in the syringe barrel 14. Moving the piston distally decreases the volume in the syringe barrel and in a closed system, increases the pressure. Moving the piston proximally increases the volume in the syringe barrel and decreases the pressure in a closed system. A plunger handle 30 is connected to the piston through the plunger shaft 32. Movement of the handle causes respective movement of the piston in the barrel.

The plunger handle 30 includes two generally rounded lateral extensions 34 extending in opposite directions from the plunger shaft 32 to form a "T" shape. The handle may be seized by an operator to disengage the syringe assembly from the mounting and driving system for manual control. A driver retainer 36 is located between the two extensions 34 of the handle 30 and is aligned with the longitudinal axis of the shaft 32. The driver retainer 36 includes two parallel prongs 37 extending proximally, each prong having a barb 38 disposed at its farthest end on the inside surface. The two parallel prongs of the driver retainer 36 define a space therebetween for accepting a drive arm 70 for controlling the position of the syringe plunger 16.

The mounting head 18 is fixedly mounted to the distal end of the syringe barrel 14 and includes a pair of rounded projections 40 located laterally on either side in respect to the syringe barrel 14. These projections 40 are shaped and sized to provide pivotal mounting for the syringe assembly in a mounting bracket as is shown and described in greater detail below. Each projection 40 as shown comprises two rounded ends 42 or ears with a connecting ridge 44 between them. The pivotal mounting arrangement with the pivot being located at one end of the syringe assembly and the point of force being applied at the other end of the assembly provides greater mechanical advantage to one attempting to remove the syringe assembly 10 from the mounting structure. While the drawings show that the mounting head 18 and the rounded mounting projections 40 are attached to the distal end of the syringe barrel, other embodiments are possible. For example, the projections may be formed as part of the syringe barrel in another configuration.

The mounting head 18 includes a circuit board 46 having open contact surfaces 48 for establishing an electrical connection between circuits in an instrument and circuits in the syringe assembly 10. One circuit in the syringe assembly is the pressure sensor 24 and in this embodiment, the pressure sensor comprises a strain beam type or piezo-resistive type sensor. The circuit board 46 has eight contact surfaces 48 although more or fewer may be required depending on the circuits contained in the syringe assembly 10. In this case, the syringe assembly includes the pressure sensor 24 and the electrical leads for a remote controller 56. A cover 50 protects the board 46 from damage. The cover 50 includes two slots 52 to permit access to the contact surfaces 48 of the circuit board 46.

The circuit board 46 includes lead wires 54 that form an electrical connection with the remote controller 56. The rigid fluid line 20 is in fluid communication with a flexible fluid line 58 that also leads to the remote controller 56 in FIG. 1. The lead wires 54 and flexible fluid line 58 are kept bundled together by a plurality of elastic bands 60. The electrical lead wires 54 terminate in the remote controller 56 while the fluid line 58 travels beyond the remote controller for eventual connection to a catheter (not shown). A slot 62 is formed in the bottom surface of the remote controller 56 along its length and the flexible fluid line 58 is mounted in that slot. The slot 62 is slightly smaller than the flexible tubing 58 and is deep enough so that once inserted, the flexible tubing tends to remain in the slot. This and the banding of the electrical lead wires with the flexible tubing have the advantageous effect of reducing the clutter by retaining the devices together.

The remote controller 56 can be operated either by the physician who also is maneuvering the proximal end of the balloon catheter as well as by an assistant who may stand near the physician without interfering with the physician's handling of the proximal end of the balloon catheter. In this case, the flexible tubing 58 would be pulled out of the slot 62 to separate it from the controller and the bands 60 moved toward the syringe assembly so that the controller 56 can be operated by the assistant while the catheter can be operated by the physician. This separated configuration is shown in FIG. 6.

The remote controller 56 includes a plurality of switches. These switches may be rocker switches, slide switches, rotary switches, non-electrical pneumatic control switches, any other types or combinations of switches for providing control signals. In this embodiment, dome switches are used that provide a mechanical feel of a click when depressed.

Figure 6:
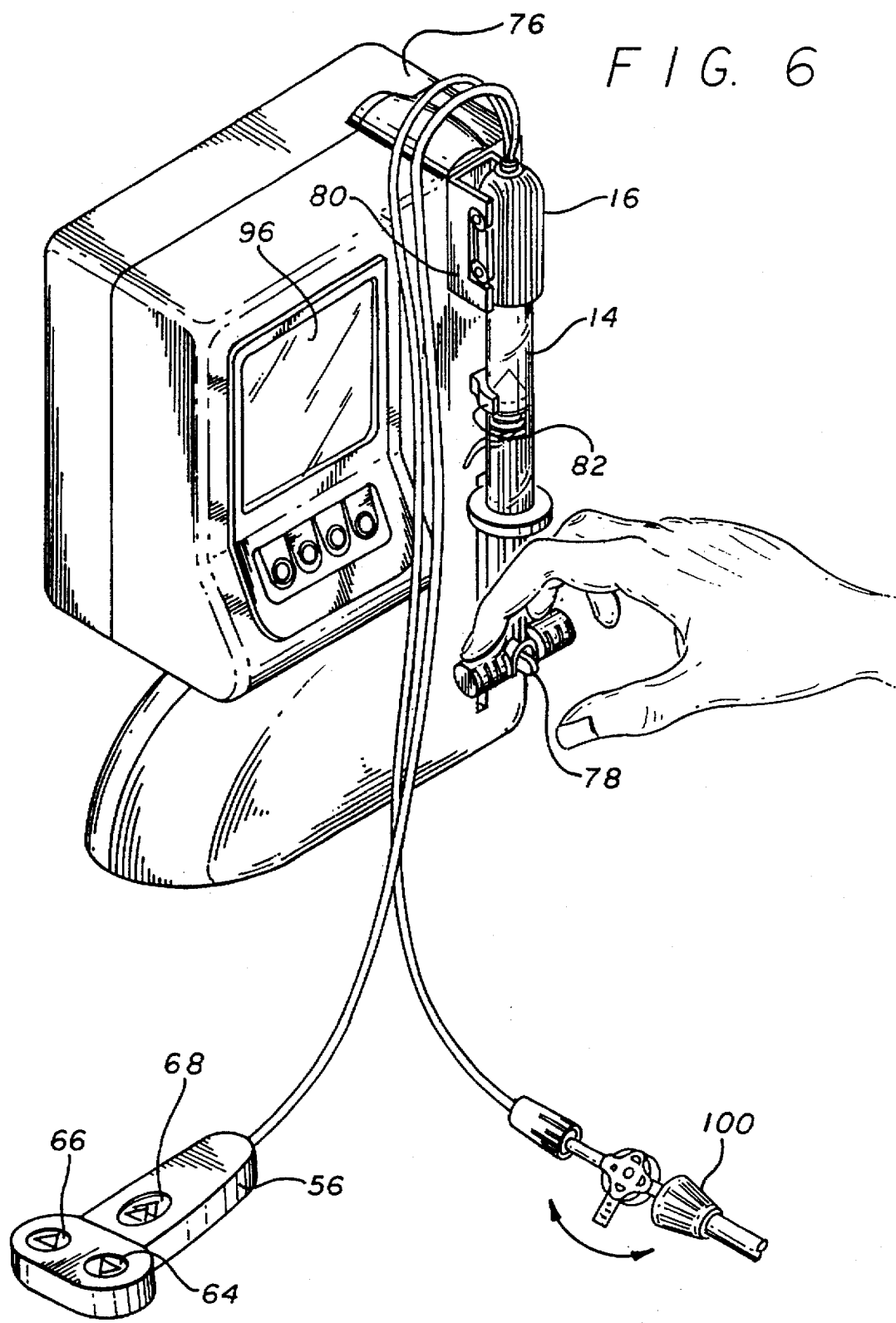
FIG. 6 shows the syringe assembly of FIG. 1 installed in the mounting bracket and clamp on the instrument and a technique for rapidly removing the syringe assembly from its mounted position.

The three switches of the remote controller 56 shown in FIG. 6 comprise an increase-pressure switch 64, a decrease-pressure switch 66, and a rapid-decrease-pressure switch 68. Should rapid deflation of the balloon be desired, the rapid decrease-pressure switch 68 may be activated to rapidly decrease the pressure in an inflatable device to, in this embodiment, a partial vacuum such as −7 psi.

A stopcock 70, or other suitable fluid control device, is located at the distal end of the flexible fluid line 58 and is secured to the fluid line by a rotating luer lock connector 72. The stopcock 64 controls the fluid communication of the fluid line 58. Three positions are shown in this case. The first position closes the fluid line so no fluid communication with any external device or line can occur. The second position vents the fluid line 58 to outside air through a vent port 74, and the third position will establish fluid communication between the fluid line 58 and a connected catheter (not shown). When the stopcock is placed in the third position, the syringe assembly 10 then will control the pressure in the catheter based on the volume of the syringe barrel. Stopcocks and luer connectors are well known to those skilled in the art and no further details are provided here.

Figure 4:
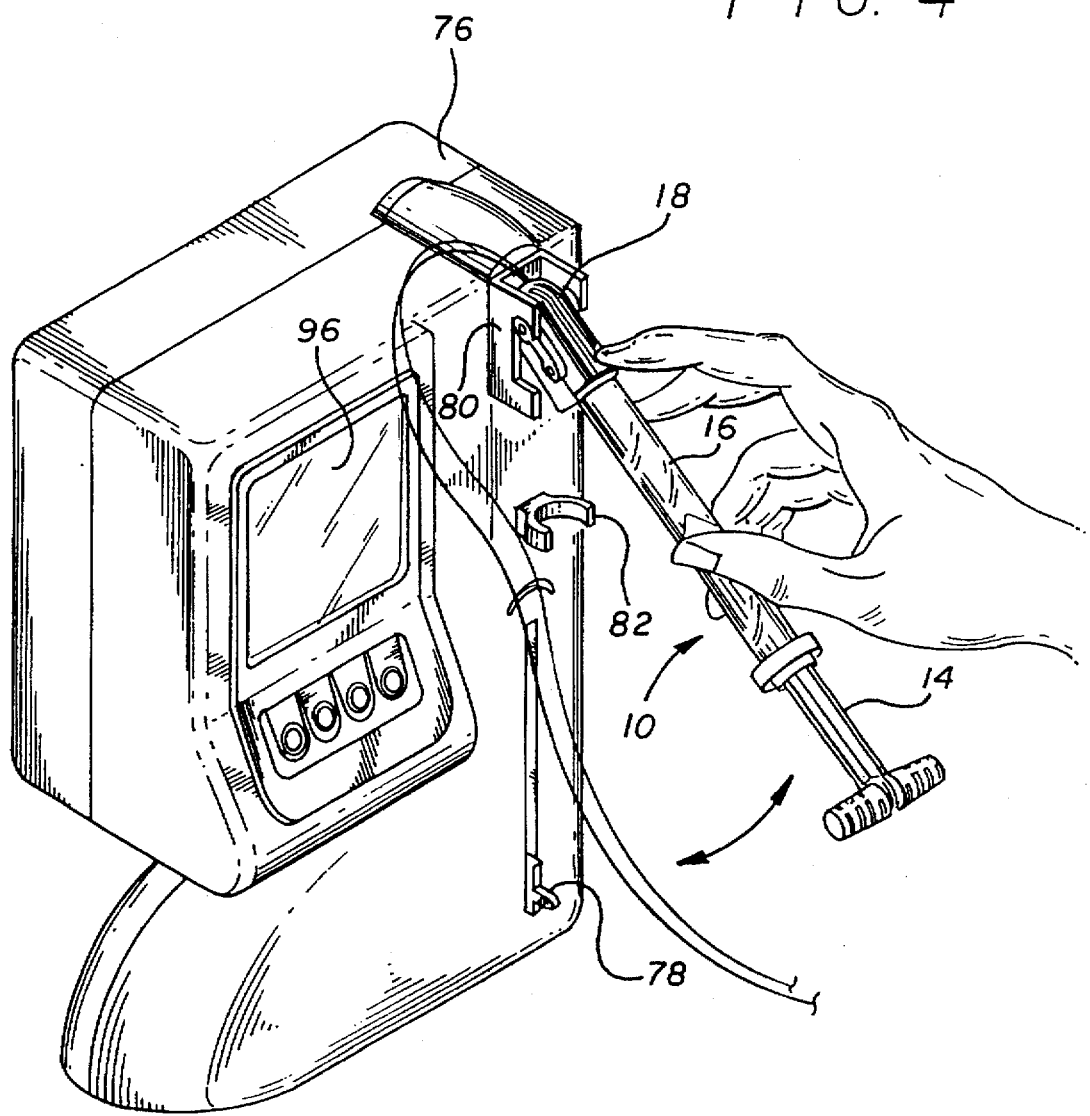
FIG. 4 is a diagrammatic view of the syringe assembly of FIG. 1 being installed into a mounting bracket, and also showing a plunger drive arm used to control the volume in the syringe.

Referring now to FIG. 4, the use of the mounting head 18 of the syringe assembly 10 of FIGS. 1 through 3 is shown. In FIG. 4, the syringe assembly 10 is being installed and mounted to an instrument 76. The instrument includes a syringe plunger drive apparatus (not shown) that has a drive arm 78 shown. The drive apparatus may be any of the well known types including a motorized lead screw using a DC motor. The drive apparatus may also be in the form of a DC servo motor, a step motor, a hydraulic motor, a pneumatic motor, or others. Whatever the specific type, the drive apparatus typically includes a moveable drive arm 78 that is capable of directing the movement of another element, such as by pushing or pulling, that it may come in contact with. The drive arm 78 is shown in a "home" position from which the drive arm is moved forward in order to engage the plunger 16 of the syringe 12, which is preferably mounted in a vertical orientation so that air bubbles can be more easily seen and eliminated. Other suitable means that can pressurize or depressurize and direct a quantity of fluid may also be used.

There exist two limits of travel for the drive arm 78 in this embodiment, an upper limit and a lower limit or the home position. In one embodiment, detectors are positioned at the limits and the drive arm has a flag associated with its movement. When the flag trips the respective detector, the position of the drive arm at the limit is detected.

The front of the instrument 76 in this case includes a mounting bracket 80 and a clamp 82 for holding the syringe assembly stationary in relation to the drive arm 78. In this case, the clamp 82 is an open C-type clamp with resilient arms that separate upon forcing the syringe barrel 14 through the opening between them and then reclose around the syringe barrel to capture it in place. The C-clamp 82 secures the syringe assembly 10 in position and opposes any force that may be developed by the drive arm 78 that may cause the syringe to eject from its mounting at the front of the instrument. The bracket 80 secures the syringe assembly from movement in the longitudinal, lateral, and rotational directions while the C-clamp secures the syringe assembly from movement in the normal direction. FIG. 4 shows the pivoting motion used to mount the syringe assembly 10 to the instrument 76. The mounting head 18 is first engaged with the mounting bracket 80 and the barrel 14 of the syringe is then placed into the C-clamp 82. As the mounting head 18 is placed into the bracket 80 and the syringe is pivoted into contact with the C-clamp 82, the spring-loaded electrical pins 86 come into contact with respective contact surfaces 48 on the circuit board 46.

Figure 5:
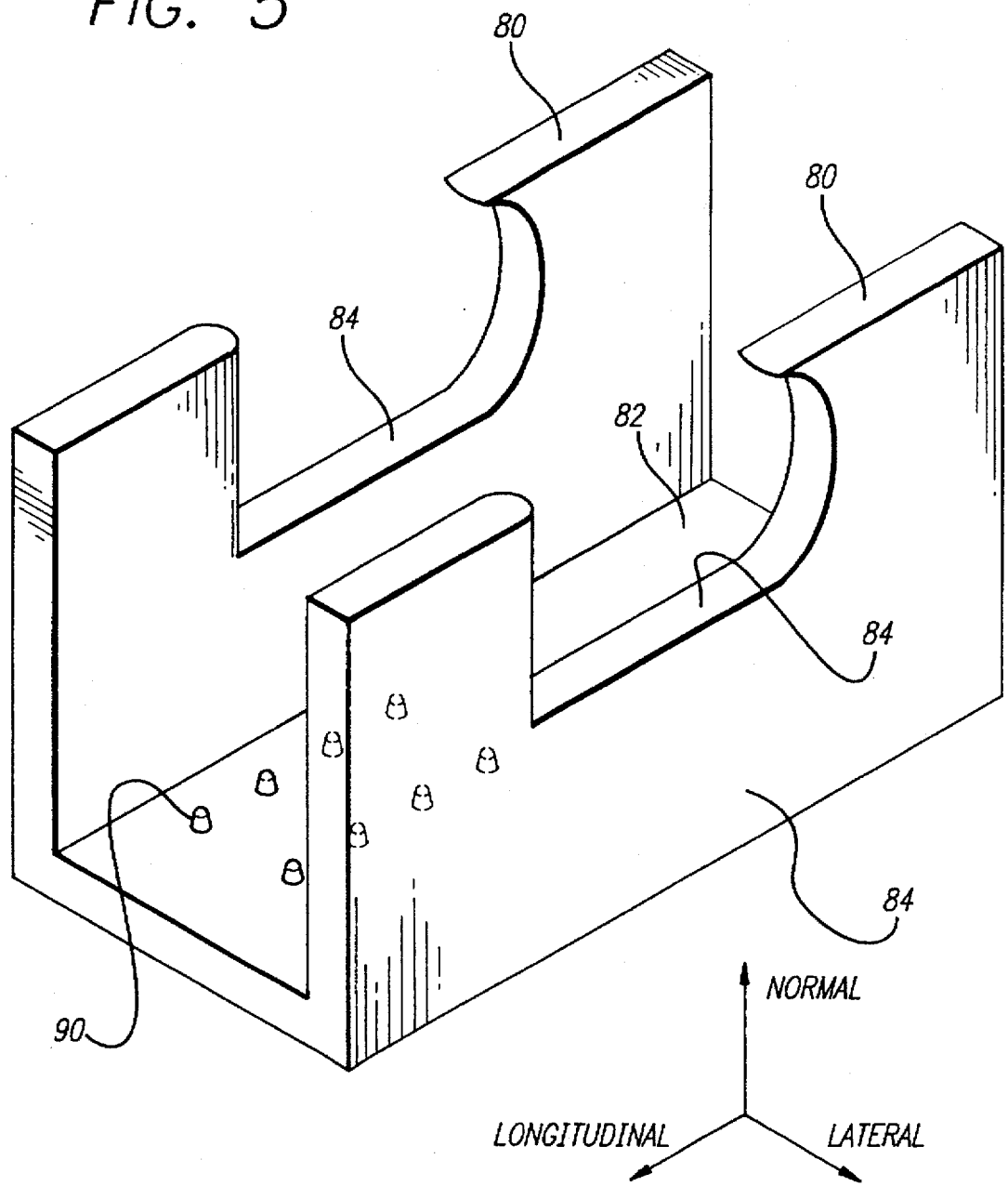
FIG. 5 is a perspective view of the mounting bracket shown in FIG. 4 for receiving the syringe assembly and showing electrical connectors for mating with the pressure sensor.

FIG. 5 shows further detail of the mounting bracket 80 that provides a pivotal connection with the mounting head 18 of the syringe assembly 10. The sidewalls 84 of the bracket 80 limit lateral movement of the syringe assembly 10 while the notches 86 limit movement in the longitudinal directions and limit rotational movement of the syringe assembly. Additionally, the curvature of the front end of the notch assists in limiting movement of the syringe assembly in the normal direction as does the C-clamp 82.

The base 88 of the mounting bracket 80 resides along a plane defined by the lateral and longitudinal axes. The plurality of electrical contacts 90 found on the base 88 are, in this embodiment, spring-biased electrical pins 90 that form a connection with the electrical contacts 48 of the circuit board 46 on a properly installed syringe assembly 10. As noted earlier, other means of contact engagement with the pressure sensor can be used and will be apparent to those skilled in the art. The mechanical action of the spring-biased pins 90 permits the pivotal mounting action to occur to obtain a proper mounting of the syringe assembly 10 to the instrument 76 while at the same time assuring electrical continuity with the circuit board 46. This technique for providing electrical contacts with the syringe assembly also acts as a security measure in that only a properly mounted syringe assembly will make electrical contact. The instrument 76 includes a circuit for determining if a syringe has been mounted properly and will not permit certain operations until a syringe is in place.

Additionally, the locations of the contact surfaces 48 and the pins 90 are off center from the longitudinal center line of the syringe assembly as can be clearly seen in FIG. 2. This also assists in the proper mounting of the syringe in that the pins will not contact the circuit board 46 contacts 48 unless the syringe is properly mounted.

Other techniques for determining if the syringe assembly has been correctly mounted may become apparent to those skilled in the art. For example, an optical system may be used that senses the presence of a tag on the syringe assembly. In another embodiment, the position of one or more of the spring-loaded pins may be monitored and when the pin or pins are moved to compress a spring, the presence of a syringe is indicated.

FIG. 6 shows a syringe assembly 10 properly installed on the instrument 76. The rounded, T-shaped handle 30 allows the operator to easily grasp the syringe assembly 10 when the need arises for removal of the syringe assembly from the instrument. As mentioned above, the pivotal mounting technique provides increased mechanical advantage in pulling the syringe barrel from the C-clamp 82. This facilitates the rapid and easy removal of the syringe assembly 10 from the instrument 76 should the need arise. When the syringe assembly is removed, the drive arm 78 is automatically moved down along the longitudinal axis to its lower limit or "home" position as shown in FIG. 4. When the drive arm reaches the home position, the instrument 76 is ready to accept the installation of the syringe assembly. The drive arm can then move forward to engage a syringe plunger.

Furthermore, as shown in FIG. 6, the syringe barrel and plunger are mounted vertically with the output of the syringe at the top. Air bubbles will rise to the top of the barrel and will be more apparent as well as easier to eliminate. Once they are at the top of the barrel, moving the plunger distally will cause them to enter the fluid line 58 where they can be purged.

Figure 7:
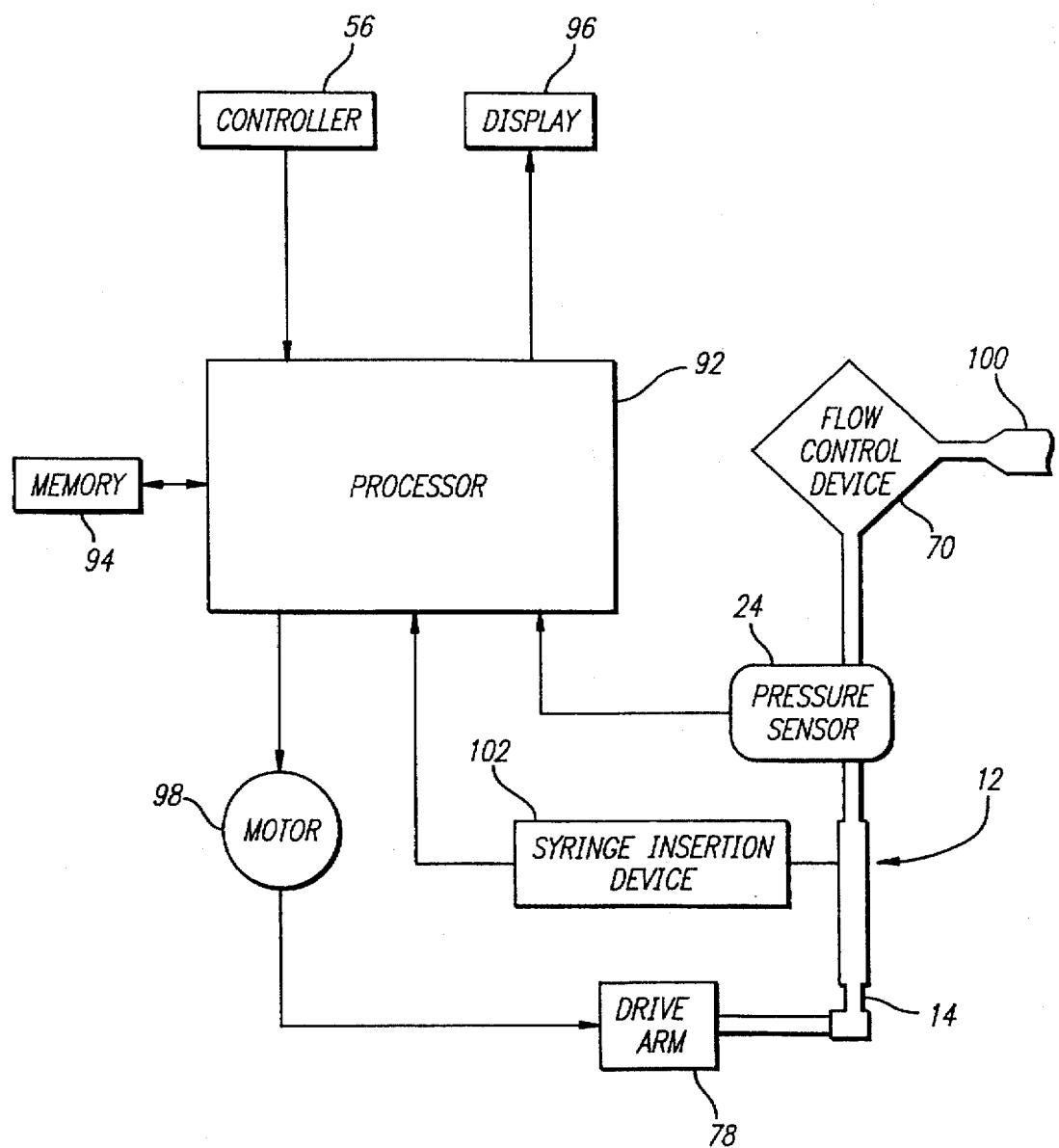
FIG. 7 is a block diagram of an automatic engagement and pressure checking system in accordance with principles of the claimed invention.

Referring now to FIG. 7, a block diagram is presented of an inflation control system. A processor 92 having a memory 94 for storing data and programs is connected to a display 96 and a controller, such as the remote controller 56 of FIG. 1. The term memory is used in a general sense and may comprise RAM, ROM, magnetic storage, or other storage media. The display 96 presents alarms as well as pressure data and other data such as the duration of each inflation, the number of inflations, and the elapsed time between inflations. Other values may be displayed as well. The controller 56 may take other forms such as front panel switches on the instrument 76 shown in FIG. 4. The processor 92 controls a motor 98 that in turn moves a drive arm 78 to move the plunger of a syringe 12. A pressure sensor 24 measures fluid pressure in the fluid line 58 and a flow control device 70, such as a stopcock, connects the fluid line 58 to a catheter 100, to a vent, or closes the line completely, as described above. A syringe insertion detector 102 is shown that detects the presence of a syringe.

After mounting a syringe assembly but before the drive arm engages the syringe assembly 10, the stopcock 70 is set to the second or "vent" position, and this condition is signaled to the processor by the operator using a preselected switch of the remote controller 56. This allows the processor to calibrate the pressure sensor 24 to ambient atmospheric pressure. The detected pressure is then stored in memory 94 for calibrating the zero pressure value for the system. After the processor receives the confirmation signal from preselected switch of the remote controller 56, the display 96 instructs the operator to then close the stopcock 70. Once this condition has been met, as indicated by a signal from the remote controller 56, the processor 92 then proceeds to move the drive arm 78 into engagement with the plunger 16.

Figure 8:
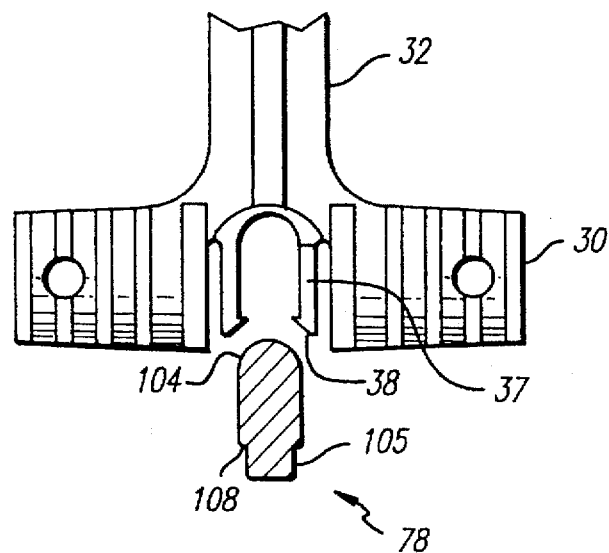
FIGS. 8, 9, and 10 are top views illustrating a sequence in which the drive arm of the syringe plunger driver apparatus engages the driver retainer of the syringe assembly.
Figure 9:
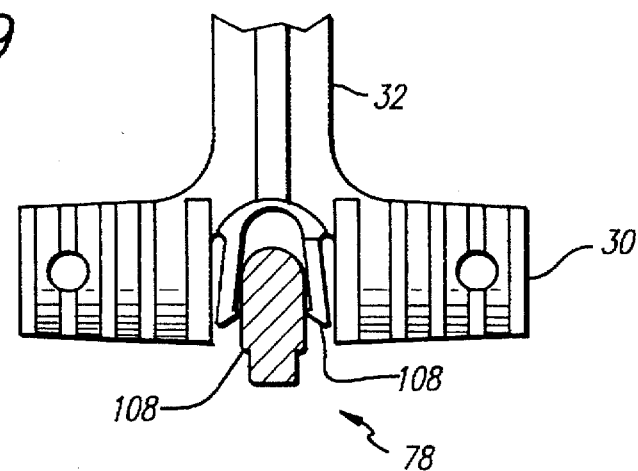
Figure 10:
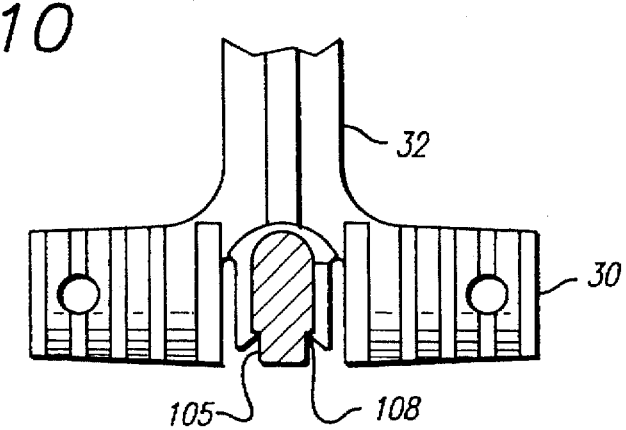

Referring now to FIGS. 8 through 10, the capture of the drive arm 78 by the driver retainer 36 of the syringe plunger handle 30 is illustrated. In FIG. 8, the drive arm 78 is moving forward along the longitudinal axis until it touches the barbs 38 of the prongs 37 of the retainer 36. In FIG. 9, the drive arm 78 has continued its longitudinal movement forcing the prongs and barbs apart to allow the drive arm to move between them. Upon moving completely between them as shown in FIG. 10, the prongs and barbs snap back into their at-rest position capturing the drive arm 78 between them. The barbs 38 of the driver retainer 36 have an inward slope which facilitates the movement of the rounded forward face of the drive arm 78 between them. The drive arm has a rounded front surface 104 to assist its movement past the barbs 38, which then snap around the recessed rear portion 105 of the drive arm 78. In this case, the drive arm 78 includes notches 108 formed about half way between the rear and front surfaces for accepting the barbs of the retainer 36. Additionally, the surface of the drive arm 78 is substantially straight and smooth in the normal direction and the surfaces of the retainer 36 are straight and smooth so that the syringe handle 30 can be easily pulled off the drive arm 78 in the normal direction in order to facilitate easy removal of the syringe assembly 10.

FIG. 11 is a front view of the instrument 76 showing the display 96. The display 96 presents both the pressure in digital form 110 and in bar graph form 112, and also presents the Inflation Time 114 and the time Between Inflations 116. As is apparent, the bar graph display 112 is graphical in nature while the digital display is numerical or digital. It has been found that a graphical display many times communicates information faster than a numerical or digital display; however, when greater accuracy is desired, the digital display would be consulted. In one embodiment, the display comprises an LCD display device which is capable of generating a variety of menu and status screens. After a syringe assembly 10 is mounted, the processor 92 monitors the inflation control signals and pressures generated to provide appropriate timing displays.

Referring now to FIG. 12, the processor initially sets the Inflation Time and the time Between Inflations to zero 120. The processor then monitors 122 for the activation of the increase-pressure switch 64. At the same time, the pressure signal from the pressure sensor 24 is monitored 124 for a pressure increase above a predetermined threshold pressure such as ten psi. Upon subsequent deactivation 126 of the increase-pressure switch, and the pressure being above the threshold, the processor causes the Inflation Time display to commence a count-up time display 128.

FIG. 13 is a flow chart describing the display of the elapsed time between inflations tied to the use of a decrease-pressure switch 66. In this embodiment, the processor 92 will not allow commencement of the display of time between inflations unless the processor has previously commenced a display of inflation time 130. The processor 92 monitors 132 for the activation of the decrease-pressure switch 66. At the same time, the pressure signal from the pressure sensor 24 is monitored 134 for a pressure decrease below a predetermined threshold pressure such as zero psi. Upon subsequent deactivation of the decrease-pressure switch 136, and the pressure being below the threshold, the processor causes the time Between Inflations to commence a count-up display 138. In this embodiment, the Inflation Time display ceases to count up 140 but continues to display the number present when the time Between Inflations display commences to count up.

As with the increase-pressure switch 64, the decrease-pressure switch 66 must be continuously depressed in this embodiment in order to continue to cause the drive arm to move. The operator releases the decrease-pressure switch 66 when the desired pressure is reached.

Figure 14:
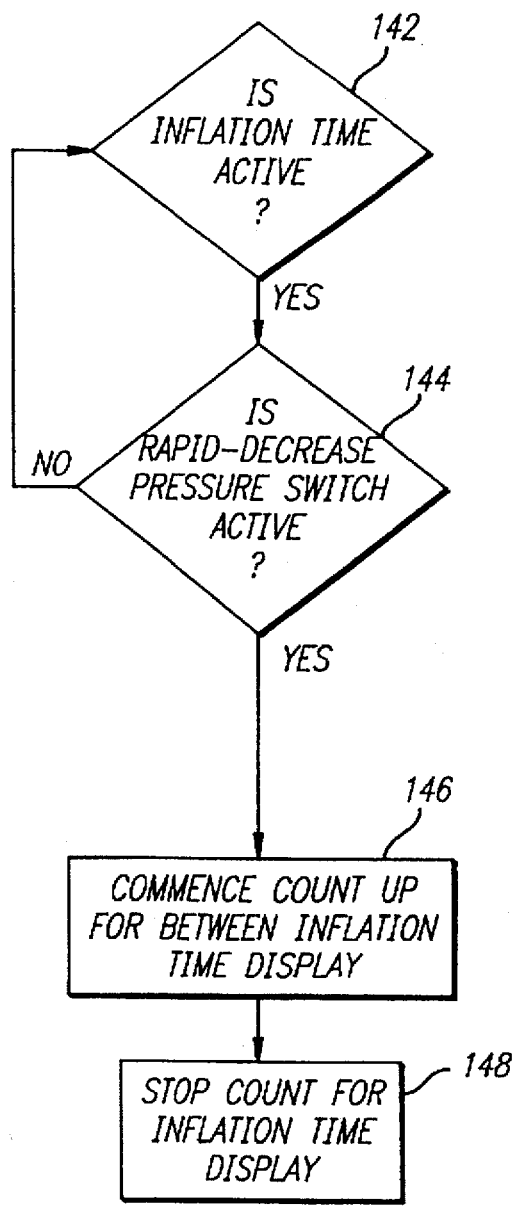
FIG. 14 is a flow chart illustrating the determination of the elapsed time between inflation cycles when a rapid pressure decrease switch is activated.

FIG. 14 presents a flow chart describing the determination and display of the elapsed time Between Inflations when the rapid decrease-pressure switch 68 is activated. As stated above, the processor 92 will not allow commencement of the display of time between inflations unless the processor has previously commenced a display of inflation time 142. The processor 92 monitors 144 for the activation of the rapid decrease-pressure switch 68. Upon detecting that activation, the processor causes the time Between Inflations to commence a count-up display immediately 146. The processor in this case does not factor in the pressure sensed before commencing the count up display. Also, the Inflation Time display ceases to count up 148 but continues to display the number present when the rapid decrease-pressure switch 68 was activated. When the rapid-decrease-pressure switch 68 is depressed, the processor controls the motor 98 to deliver full power output to rapidly move the drive arm 78 and the engaged plunger 16 in a reverse direction in order to deflate the balloon catheter rapidly. The response of the processor to the activation of the rapid decrease-pressure switch 68 is a latching type response in that the switch does not need be held down continuously. Once activated, the processor controls the motor until a predetermined pressure threshold has been reached, such as −7 psi.

Once again activating the increase-pressure switch 64 to cause the pressure to exceed the threshold described above, i.e., ten psi, will cause the processor to reset the Inflation Time display to zero once the increase-pressure switch has thereafter been deactivated. The processor will then cause the display to count up as described above. The time Between Inflations will cease to count up and will retain its last count when the Inflation Time began to count up once again.

Figure 15:
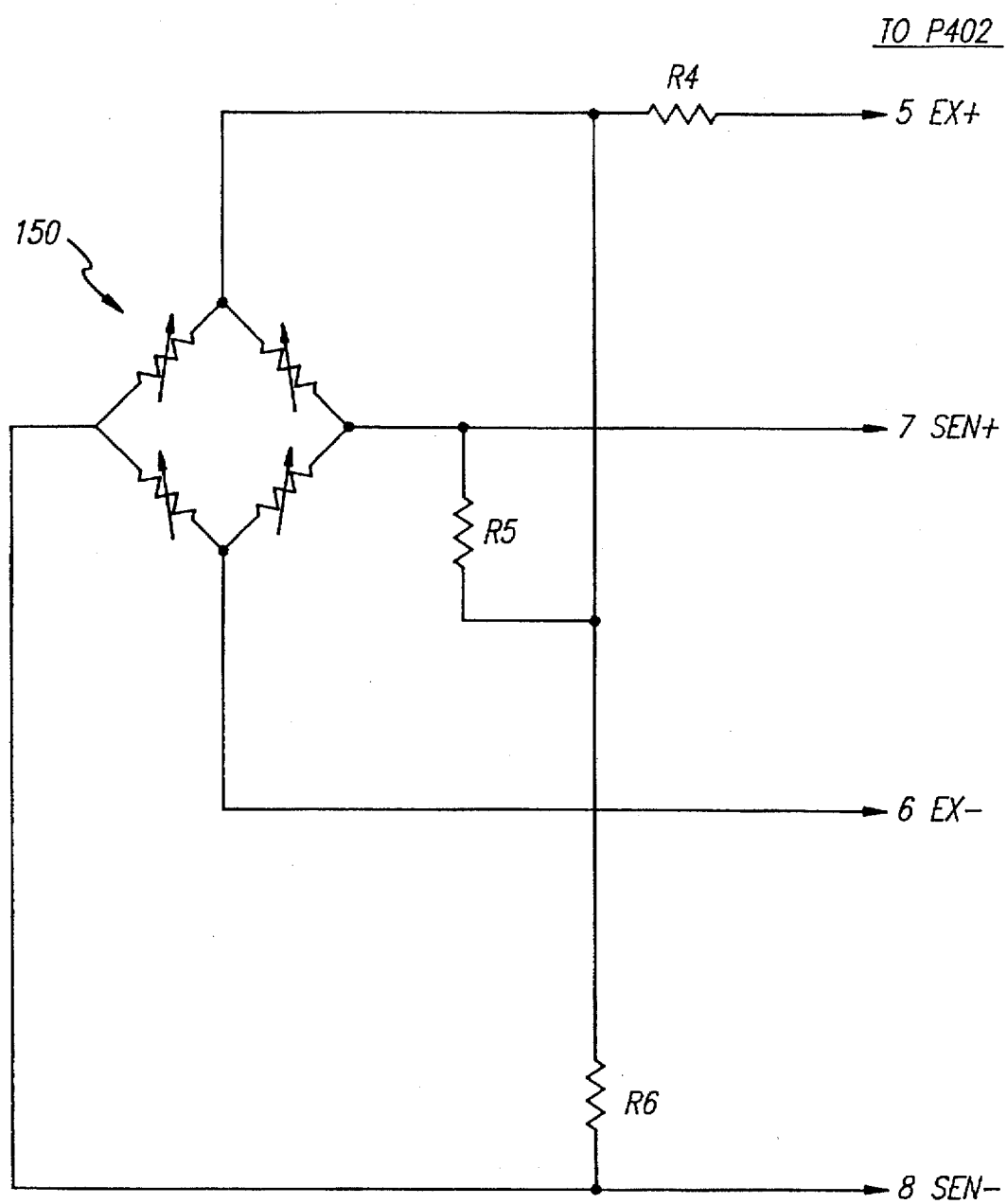
FIG. 15 is circuitry for a pressure sensor.

A pressure sensor is presented in FIG. 15 consisting of a Wheatstone bridge circuit 150 with trim resistors R4, R5, and R6. The operation of this sensor is well known to those skilled in the art.

Figure 16A:
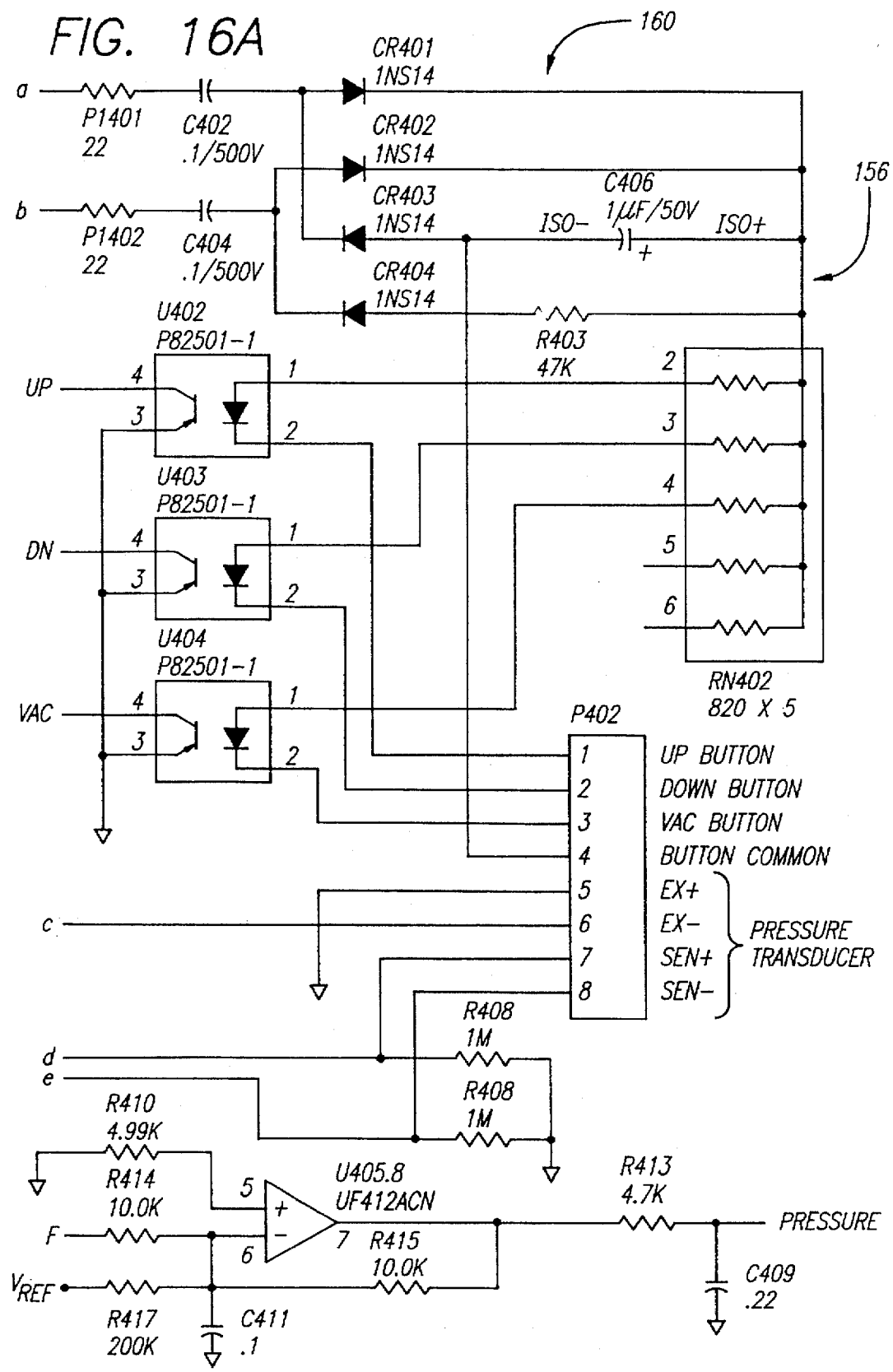

In FIGS. 16A and 16B, circuit diagrams are presented of a pressure signal processor 152 usable in the systems described above, the operation of which is apparent to those skilled in the art. An unbalance in the bridge circuit of the pressure sensor 150 causes the levels on the inverting and noninverting inputs of U405 to differ thus causing an output signal. That output signal is provided to U405-B which provides offset. A PRESSURE signal is provided for use by the processor 92. The level of the PRESSURE signal represents the pressure sensed by the pressure sensor 150.

To sense the existence of a syringe assembly, a syringe insertion detector 154 in the instrument is used. The syringe insertion detector 154 functions by detecting current across the EX+ and EX– lines. If a sensor is present, the Wheatstone bridge circuit 150 of that sensor completes the current circuit and transistor Q402 will be turned on. Transistor Q402 thus senses current flow. The device U405A controls the voltages used for the pressure sensor and transistor Q401 controls the output voltage to indicate to the processor as signal DISP-INS that a syringe is or is not present in response to transistor Q402 being turned on or off.

In the above embodiment, the Wheatstone bridge circuit 150 forming a part of the pressure sensor mounted in the syringe assembly functions as a syringe insertion device. Its electrical connection to P402 indicates the presence of a properly mounted syringe. Other embodiments are possible, including magnetic devices and optical devices as well as different electrical circuits.

Additionally, power and isolation circuits 156 for the switches of the remote controller 56 are shown. Optical isolators U402, U403, and U404 isolate the remote controller from processor voltages. The UP, DN, and VAC signals are used by the processor as discussed above. The power circuit 158 provides a floating power source for the switches of the controller 56. The U401:A and U401:B devices create an oscillator with the diode circuit 160 rectifying the power created. The floating power circuit 158 isolates the remote controller 56 from ground and from DC sources via capacitors C402 and C404. This feature provides increased protection for persons coming in contact with the controller 56.

The LF353N devices and the LF412ACN devices may be obtained from National Semiconductor. The INA114AP device may be obtained from Burr-Brown, and the PS205-1 devices may be obtained from NEC.

From the above, it is evident that the present invention provides for an advantageous design for automatically timing the Inflation cycles and the time Between Inflations of a syringe assembly installed in an inflation control system. While several particular forms of the invention have been illustrated and described, it also will be appreciated that various modifications can be made to the present invention without departing from the spirit and scope thereof.

The following pages comprise an embodiment of a computer program used to implement the above features.

© COPYRIGHT Advanced Cardiovascular Systems, Inc. 1994, 1995

All Rights Reserved

Unpublished Work

What is claimed is:

1. A system for controlling the inflation of an inflatable device and for measuring elapsed time during inflation control, the system comprising:

an inflation medium disposed in the inflatable device, the extent of inflation controlled by the pressure of the inflation medium;

a sensor that senses the pressure of the inflation medium and provides a pressure sense signal;

a manually operable pressure-decrease switch that provides a pressure decrease control signal;

a pressure control device that receives the pressure sense signal and the pressure decrease signal, controls the pressure of the inflation medium in response to the pressure decrease control signal, and provides a timer activation signal;

a timer that receives the timer activation signal, measures elapsed time, and provides a time signal; and a display that receives the time signal and displays the elapsed time based on the time signal;

wherein the timer begins timing elapsed deflation time after the pressure-decrease switch has been activated, the pressure sense signal indicates that the pressure of the inflation medium has reached a predetermined threshold, and the pressure-decrease switch is then inactivated; and wherein the display displays the elapsed inflation time.

2. The system of claim 1 wherein the predetermined threshold is approximately zero psi.

3. The system of claim 1 further comprising:

a manually operable rapid pressure-decrease switch that provides a rapid pressure-decrease control signal to the pressure control device;

wherein the timer begins timing elapsed deflation time after the rapid pressure-decrease switch has been activated.

4. The system of claim 3 further comprising:

a manually operable pressure-increase switch that provides a pressure increase control signal to the pressure control device;

wherein the timer begins timing elapsed inflation time upon activation of the pressure increase switch;

wherein the timer begins timing elapsed deflation time if the timer is currently timing elapsed inflation time and the rapid pressure-decrease switch has been activated.

5. The system of claim 1 further comprising:

a manually operable pressure-increase switch that provides a pressure increase control signal to the pressure control device;

wherein the timer begins timing elapsed inflation time upon activation of the pressure increase switch;

wherein the timer begins timing elapsed deflation time if the timer is currently timing elapsed inflation time, and the pressure-decrease switch has been activated, the pressure sense signal indicates that the pressure of the inflation medium has reached a predetermined threshold, and the pressure-decrease switch is then inactivated.

6. The system of claim 1, wherein the manually operable pressure decrease switch is configured to be activated and inactivated by a user.

7. A system for controlling the inflation of an inflatable device, the system comprising:

an inflatable device containing an inflation medium therein;

a sensor that monitors the pressure of the inflation medium in the inflatable device and provides a corresponding pressure sense signal;

a pressure control switch configured to provide a first pressure control signal;

a pressure control device configured to receive the pressure sense signal and the first pressure control signal, control the pressure of the inflation medium in response to the first pressure control signal, compare the pressure sense signal to a first threshold value, and provide a first timer activation signal;

a timer that receives the first timer activation signal, measures elapsed time, and provides a corresponding first time signal;

a display configured to receive the first time signal, wherein the display is configured to display a first indication of elapsed time based on the first time signal.

8. The system of claim 7, wherein the first pressure control signal comprises a pressure decrease control signal, and the pressure control device is configured to reduce the pressure of the inflation medium in response to the pressure decrease control signal.

9. The system of claim 7, wherein the first pressure control signal comprises a pressure increase control signal, and the pressure control device is configured to increase the pressure of the inflation medium in response to the pressure control signal.

10. The system of claim 7, wherein the pressure control switch is configured to provide a second pressure control signal; the pressure control device is configured to receive the second pressure control signal, control the pressure of the inflation medium in response to the second pressure control signal, compare the pressure sense signal to a second threshold value, and provide a second timer activation signal; the timer is configured to receive the second timer activation signal, measure elapsed time, and provide a corresponding second time signal; and the display is configured to receive the second time signal and display a second indication of elapsed time based on the second time signal.

11. The system of claim 10, wherein the first pressure control signal comprises a pressure decrease control signal, and the second pressure control signal comprises a pressure increase control signal.

12. The system of claim 7, wherein the pressure control switch comprises a manually operable pressure control switch having an activated configuration and a deactivated configuration, and the first pressure control signal comprises a deactivated control signal when the pressure control switch is in the activated configuration, and the pressure control signal comprises a deactivated control signal when the pressure control switch is the deactivated configuration.

13. The system of claim 12, wherein the pressure control device is configured to provide the first timer activation signal if and only if the pressure signal has reached the first threshold value and the pressure control switch is providing a deactivated control signal.

* * * * *

UNITED STATES PATENT AND TRADEMARK OFFICE
CERTIFICATE OF CORRECTION

PATENT NO. : 5,749,853
DATED : May 12, 1998
INVENTOR(S) : Joseph A. O'Donnell, Douglas R. Hamper It is certified that error appears in the above-identified patent and that said Letters Patent is hereby corrected as shown below:

FIG. 16A, Sheet 12 of 13, change "U405.8", to read --U405:B--.

FIG 16A, Sheet 12 of 13, change "F", to read --f--.

FIG 16B, Sheet 13 of 13, change "C", to read --c--.

Column 10, Line 60, change "U405", to read --U408--.

Column 10, Line 61, change "U405-B", to read --U405:B--.

Column 11, Line 4, change "U405A", to read --U406:A--.

Signed and Sealed this

Sixteenth Day of March, 1999

Attest:

Q. TODD DICKINSON

Attesting Officer

Acting Commissioner of Patents and Trademarks